(12) United States Patent
Ohkawa

(10) Patent No.: US 6,805,783 B2
(45) Date of Patent: Oct. 19, 2004

(54) METHOD FOR MANIPULATING A SOLUTION USING A FERROELECTRIC ELECTRO-OSMOTIC PUMP

(75) Inventor: Tihiro Ohkawa, La Jolla, CA (US)

(73) Assignee: Toyo Technologies, Inc., La Jolla, CA (US)

( * ) Notice: Subject to any disclaimer, the term of this patent is extended or adjusted under 35 U.S.C. 154(b) by 552 days.

(21) Appl. No.: 09/735,985

(22) Filed: Dec. 13, 2000

(65) Prior Publication Data

US 2002/0070116 A1 Jun. 13, 2002

(51) Int. Cl.[7] ............................ G01N 27/26; F04B 37/02
(52) U.S. Cl. ..................... 204/454; 204/450; 204/451
(58) Field of Search .................... 204/450, 451, 204/454, 600, 601, 604, 608, 609; 417/48, 53, 62, 426

(56) References Cited

U.S. PATENT DOCUMENTS

| | | | |
|---|---|---|---|
| 3,505,634 A | | 4/1970 | Von Vick |
| 3,930,982 A | * | 1/1976 | Batha et al. ................. 204/660 |
| 4,278,085 A | | 7/1981 | Shim |
| 4,309,908 A | | 1/1982 | Rapp |
| 4,445,826 A | | 5/1984 | Tarr |
| 4,482,347 A | | 11/1984 | Borsanyi |
| 4,702,675 A | | 10/1987 | Aldrovandi |
| 4,908,112 A | * | 3/1990 | Pace ........................ 210/198.2 |
| 5,092,972 A | * | 3/1992 | Ghowsi ....................... 204/454 |
| 5,151,164 A | * | 9/1992 | Blanchard et al. ........... 204/451 |
| 5,240,585 A | * | 8/1993 | Young et al. ................ 204/601 |
| 5,262,031 A | * | 11/1993 | Lux et al. .................... 204/601 |
| 5,282,942 A | * | 2/1994 | Herrick et al. ............... 204/454 |
| 5,320,730 A | * | 6/1994 | Ewing et al. ................ 204/603 |

FOREIGN PATENT DOCUMENTS

WO        WO 00/22427 A1 *   4/2000    ......... G01N/27/447

* cited by examiner

*Primary Examiner*—Nam Nguyen
*Assistant Examiner*—Brian L. Mutschler
(74) *Attorney, Agent, or Firm*—Nydegger & Associates

(57) ABSTRACT

A device and method for pumping an electrolyte solution includes a conduit having a first end, a second end and a lumen for containing the electrolyte solution. An opening at each end of the conduit allows electrolyte solution to enter and exit the lumen of the conduit. The device further includes a ferroelectric member that is positioned along a portion of the conduit. The ferroelectric member is formed with a contact surface for interaction with the electrolyte solution. An electrode is positioned adjacent to the ferroelectric member to polarize the ferroelectric member and charge the contact surface. Driving electrodes are positioned to establish a potential difference in the electrolyte solution across the portion of the conduit containing the ferroelectric member.

3 Claims, 3 Drawing Sheets

METHOD FOR MANIPULATING A SOLUTION USING A FERROELECTRIC ELECTRO-OSMOTIC PUMP

FIELD OF THE INVENTION

The present invention pertains generally to devices for controlling the movement of electrolyte solutions. More particularly, the present invention pertains to electro-osmotic pumps. The present invention is particularly, but not exclusively, useful for an electro-osmotic pump that creates a charged surface with a ferroelectric material.

BACKGROUND OF THE INVENTION

The electro-osmotic effect can be employed to pump or otherwise control the movement of electrolyte solutions. Devices utilizing the electro-osmotic effect are particularly applicable in micro-fluidics where the manipulation of small amounts of electrolyte solution is required to perform chemical or biochemical reactions. These micro-fluidic processes are often carried out on "biochips" or "bioarrays" and have found increasing usage because only small quantities of reactants and enzymes are needed to conduct each analysis.

To explain the electro-osmotic effect, consider an electric field applied to an electrolyte solution. The electrolyte solution generally contains positive ions, negative ions and a medium for the ions such as water. When the electric field is applied to the electrolyte solution, the positive ions receive a force in the direction of the electric field. Likewise, the negative ions receive a force that is equal in magnitude to the force received by the positive ions, but applied in a direction opposite to the force on the positive ions. The result is that the solution as a whole receives a net force of zero, and the electrolyte solution as a whole does not flow. To summarize, the mere placing of an electrolyte solution in an electric field does not produce an electro-osmotic effect.

Now consider the introduction of a charged surface into the electrolyte solution. Depending on whether the charged surface is acidic (negatively charged) or caustic (positively charged), the charged surface will attract either positive or negative ions from the solution. When an electric field is applied parallel to the charged surface, the resulting electric force acting on the ions that are bound to the charged surface is generally transmitted to the charged surface. On the other hand, the oppositely charged ions (those ions not attracted to the charged surface) are free to move under the influence of the electric field. This electro-osmotic effect causes the solution to receive a net force from the applied electric field, which in turn causes the solution to flow. The direction of flow depends on the polarity of the charged surface, as well as the direction of the applied electric field.

It is known that the electro-osmotic effect can be used to effectuate a simple fluid pump. For example, a pair of electrodes (driving electrodes) can be inserted into the lumen of a tube for contact with an electrolyte solution to create an electric field along the length of the tube. In this arrangement, the inner wall of the tube can be coated with an acidic or caustic material that attracts positive or negative ions from the solution. A voltage source can then be activated to create a potential difference between the electrodes. In response, the solution will flow along the length of the tube. Note that for the simple pump described in this example, the solution will not flow in response to an alternating current (AC) applied to the electrodes, because the time-averaged force on the ions that are not attracted to the tube wall will be zero.

Electrophoresis is often used to separate charged macromolecules (by migration) from a stagnant or non-flowing solution. In these electrophoresis operations, the electro-osmotic effect is undesirable because it causes the solution to flow. To avoid the electro-osmotic effect, the vessel wall can be coated with a passivating material such as Teflon® which does not interact with either the positive ions or the negative ions.

The present invention recognizes that a ferroelectric material can be used to create the charged surface that is required to produce the electro-osmotic effect. By 'temporarily' applying an electric field to the ferroelectric material, the ferroelectric material can be 'permanently' polarized allowing creation of a charged surface for a device featuring an electro-osmotic effect. Subsequently, the ferroelectric material can be depolarized to create a passivated surface and thereby eliminate any electro-osmotic effect within the device. Depending on the application, the ferroelectric surface can be polarized to produce a surface that either attracts positive ions or negative ions. Further, the magnitude of polarization and thus the total charge placed on the ferroelectric surface can be varied during the operation of the device.

Importantly, as detailed further below, the use of a ferroelectric material allows an electro-osmotic effect to be created when an AC current is applied to the driving electrodes. When an AC current is used, the driving electrodes are not necessarily required to be in direct contact with the electrolyte solution. Rather, a dielectric material can be interposed between the driving electrode and the solution. This is particularly advantageous in situations where direct contact between the electrodes and the solution may be detrimental due to electrochemical reactions at the surface of the electrodes.

Ferroelectric materials differ from ordinary dielectric materials. In an ordinary dielectric material, the electric displacement, D, is generally proportional to the electric field, E. The ratio of the electric displacement and the electric field being the dielectric constant $\epsilon$. Since the relationship between the electric displacement, D, and the electric field, E, is linear, an ordinary dielectric material does not retain an electric displacement after removal of an electric field.

The ferroelectric material is analogous to the more familiar ferromagnetic materials such as ferromagnetic iron except the magnetic field and the magnetic induction are replaced by the electric field, E, and the electric displacement, D. The relationship between the electric field, E and the electric displacement, D, of the ferroelectric material is depicted in FIG. 1. In FIG. 1, point "a" shows the ferroelectric material in the non-polarized state with E=0 and D=0. When a positive electric field is applied and increased, the relationship between D and E follows the curve from point "a" to point "b" where a maximum displacement $D_{MAX}$ occurs. A subsequent decrease in the electric field, E, causes the displacement, D, to decrease along the curve between points "b" and "c". At point "c," the electric field, E, is zero but the displacement, D, is finite. This is the 'poled' state and the value of D at point "c" is known as the remnant polarization. A subsequent reversal of the electric field causes the remnant polarization to vanish (moving along the curve from point "c" to point "d" in FIG. 1). The relationship between E and D then follows a typical hysteresis curve, passing through points "e," "f" and "g" as shown in FIG. 1.

The remnant polarization of a ferroelectric material can be removed by a method similar to the depolarization of a magnet. Specifically, when an alternating electric field of decreasing amplitude is applied, the area enclosed by the hysteresis curve becomes smaller and smaller as the amplitude of the alternating electric field is decreased. Eventually, the remnant polarization decreases to zero and the ferroelectric material returns to its original unpolarized state (point "a" in FIG. 1).

A wide range of the ferroelectric materials are available, including the metal-titanates such as barium-titanate, metal-tantalates, metal-niobates and metal-tungstates. Ferroelectric materials are known that have a maximum displacement of several tenths of Coulomb per square meter. When these ferroelectric materials are polarized, a surface charge of about 10% of available surface lattice sites can result.

When a ferroelectric material is used as the tube material in the simple fluid pump example described above, the electro-osmotic force F that the fluid receives is given by $$F = 2\pi a L D E_d \quad [1]$$

where a is the radius of the tube, L is the length of the ferroelectric tube, D is the electric displacement after poling and $E_d$ is the driving electric field. The electro-osmotic force is balanced against the viscous force when the fluid flows at the average velocity of <V> in the tube of the length L'. We obtain $$<V> = [aL/4L'][DE_d/v] \quad [2]$$

where v is the viscosity of the fluid. A set of example parameters may be $v=10^{-3}$ kg m$^{-1}$s$^{-1}$, a=1 mm, [L'/L]=10, D=0.01 coulomb/m$^{-2}$ and $E_d$=100 v/m. The velocity is <V>=2.5 cm/s.

As discussed above, in certain situations it may be desirable to avoid direct contact between the driving electrodes and the electolyte solution. In this case it is possible to interpose a dielectric material between the driving electrodes and the electrolyte solution. When this is done, an AC voltage can be applied to the driving electrodes, and the ferroelectric material can be continuously exposed to an alternating electric field to create an electro-osmotic force.

Referring again to FIG. 1, it can be seen that for a given value of the electric field, E, the displacement, D, of the ferroelectric material is different from that of the dielectric material. Therefore, the surface charge on the ferroelectric material and the dielectric material will have a different magnitude and will not cancel each other. Thus, the fluid will have net free charge and the application of an AC driving electric field will result in an electro-osmotic force. The effective displacement $D_{eff}$ can be defined by $$D_{eff} = D - E D_{max}/E_{max} \quad [3]$$

where $D_{max}$ and $E_{max}$ are defined in FIG. 1. The effective displacement, $D_{eff}$, (which already accounts for the presence of the dielectric surface) can be used to calculate the electro-osmotic effect.

Although the hysteresis curves generally vary among different ferroelectric materials, the specific hysteresis curve for the actual ferroelectric material used in a device can be used to calculate the effective displacement, $D_{eff}$. For example, the hysteresis curve shown in FIG. 1 from point "e" to point "b" can be assumed to have the form $$D = D_{max} - \{4D_{max}^2 - [\epsilon^* E + D_{max}]^2\}^{1/2} \quad [4]$$

and from point "b" to point "e,"

$$D = -D_{max} + \{4D_{max}^2 + [\epsilon^* E - D_{max}]^2\}^{1/2} \quad [5]$$

where $\epsilon^* = D_{max}/E_{max}$. Accordingly the effective displacements are given by $$D_{eff} = D_{max} - \epsilon^* E - \{4D_{max}^2 - [\epsilon^* E + D_{max}]^2\}^{1/2} \quad [6]$$

and $$D_{eff} = D_{max} - \epsilon^* E + \{4D_{max}^2 - [\epsilon^* E - D_{max}]^2\}^{1/2} \quad [7]$$

If an AC electric field given by $$E = E_{max} \cos \omega t \quad [8]$$

is applied, where ω is the angular frequency, the effective displacements in each half cycle become $$D_{eff} = D_{max}[1 - \cos \omega t - \{4 - [1 + \cos \omega t]^2\}^{1/2}] \quad [9]$$

for $-\pi \leq \omega t \leq 0$ $$D_{eff} = D_{max}[-1 - \cos \omega t + \{4 - [1 - \cos \omega t]^2\}^{1/2}] \quad [10]$$

for $0 \leq \omega t \leq \pi$

The amplitude and the phase of the Fourier component at the frequency ω is given by $$D_{eff} = 0.76 D_{max} \cos[\omega t + \alpha] \quad [11]$$

with α=73.3°. The numerical coefficient and the value of the phase angle are associated with the particular hysteresis characteristics that were assumed.

By applying the driving electric field at the same frequency, ω, but with different phase β, namely $E_d \cos[\omega t + \beta]$. The force F on the fluid is given by $$F = 2\pi a L D_{max} E_d [0.76] \cos[\omega t + \alpha] \cos[\omega t + \beta] \quad [12]$$

and the time averaged force <F> becomes $$<F> = 2\pi a L D_{max} E_d [0.38] \cos[\alpha - \beta] \quad [13]$$

This relationship indicates that the force is maximum in one direction when β=α and a maximum in the opposite direction when β=α+π. Also, this relationship indicates that the magnitude and the direction of the force, <F>, can be controlled by adjusting the phase β.

The fluid velocity is given by $$<v> = [aL/4L'][D_{max} E_d/v][0.38] \cos[\alpha - \beta] \quad [14]$$

Further, the frequency, ω, of the A.C. poling electric field and the driving electric field can be chosen so that the capacitive impedances of the poling and the driving electrodes are comparable to the resistive impedance of the solution.

The electric resistance, R, between the driving electrodes is given by $$R = \eta L/[\pi a^2] \quad [15]$$

where η is the resistivity of the solution. The capacitance, C, of the poling electrodes is given by $$C \sim [2\pi a L/d][D_{max}/E_{max}] \quad [16]$$

where d is the thickness of the dielectric layer. By equating two impedances, $$\omega \sim [CR]^{-1} \approx [da]/[2L^2 \eta D_{max}/E_{max}] \quad [17]$$

Since the dielectric constant of the dielectric material is much smaller than the dielectric constant $D_{max}/E_{max}$ of the ferroelectric material by a factor of a hundred or more, the capacitance of the driving electrode can be made comparable to that of the poling electrode by choosing the thickness of the dielectric film a hundred times smaller than the thickness of the ferroelectric material.

In light of the above it is an object of the present invention to provide devices suitable for applying an electro-osmotic force to a electrolyte solution to pump the solution through a conduit. It is another object of the present invention to provide an electro-osmotic pump which utilizes a ferroelectric material to create a charged surface thereby allowing the surface to be charged and discharged by the application of an electric field. It is yet another object of the present invention to provide an electro-osmotic pump in which the driving electrodes are not in direct contact with the electrolyte solution. It is yet another object of the present invention to provide a miniaturized device that can forward pump, reverse pump or stop an electrolyte solution in a conduit in response to an electrical signal or voltage. A further object of the present invention is to provide a micro-fluidic network of miniaturized fluid switches that can be manipulated like an electronic circuit. Yet another object of the present invention is to provide a ferroelectric electro-osmotic pump which is easy to use, relatively simple to manufacture, and comparatively cost effective.

SUMMARY OF THE PREFERRED EMBODIMENTS

The present invention is directed to a device and method for controlling the movement of an electrolyte solution. For the present invention, the device includes a conduit having a first end, a second end and a lumen for containing the electrolyte solution. An opening at each end of the conduit allows electrolyte solution to enter and exit the lumen of the conduit. The device further includes a ferroelectric member that is disposed along a portion of the conduit, between the ends of the conduit. The ferroelectric member is formed with a contact surface for interaction with the electrolyte solution. For the present invention, the ferroelectric member is positioned along a portion of the conduit and is oriented to allow the contact surface to interact with the electrolyte solution in the lumen of the conduit.

A polarizing electrode is positioned adjacent to the ferroelectric member to establish an electric field within the ferroelectric member. For the present invention, the polarizing electrode is electrically connected to a voltage source. When activated, the voltage source causes an electric field to be generated in the ferroelectric member that polarizes the ferroelectric member. The polarizing electrode is configured and oriented relative to the ferroelectric member to establish a charge on the contact surface of the ferroelectric member when the ferroelectric member is polarized. The polarity and magnitude of the charge placed on the contact surface will depend on the polarity and magnitude of the voltage supplied to the polarizing electrode.

Driving electrodes are provided to establish a potential difference in the electrolyte solution. The driving electrodes are positioned along the conduit to establish a potential difference across the portion of the conduit containing the ferroelectric member. Specifically, one driving electrode is positioned between the first end of the conduit and the ferroelectric member, and the other driving electrode is positioned between the second end of the conduit and the ferroelectric member.

In one embodiment of the present invention, a first direct current (DC) voltage source is used to polarize the ferroelectric member. Specifically, the first DC voltage source can be used to place a charge on the polarizing electrode, which in turn, can establish an electric field in the ferroelectric member. As discussed above, due to the shape and orientation of the polarizing electrode relative to the ferroelectric member, an electric field can be established that is oriented within the ferroelectric member to create a charge on the contact surface of the ferroelectric member.

In this embodiment of the present invention, the driving electrodes are positioned in direct electrical contact with the electrolyte solution. Further, for this embodiment, a pair of direct current (DC) voltage sources can be used to establish a potential difference between the first driving electrode and the second driving electrode. The potential differential between electrodes creates a potential difference in the electrolyte solution, which in turn, applies a force on the charged ions in the electrolyte solution.

For the operation of this embodiment, the first DC voltage source is connected to the polarizing electrode and activated to polarize the ferroelectric member and thus create a charge on the contact surface. Once the ferroelectric member is polarized, the first voltage source can be deactivated. Ions in the electrolyte solution having a charge polarity that is opposite to the charge polarity of the contact surface will be attracted to the contact surface. Once the ferroelectric member is polarized, the pair of DC voltage sources can be connected to the driving electrodes to establish a potential difference in the electrolyte solution across the portion of the conduit containing the ferroelectric member. Upon establishment of the potential difference in the electrolyte solution, the electrolyte solution will flow along the conduit. The direction of flow can be reversed by reversing the polarity of the driving electrodes or the polarity of the contact surface. The flow can be slowed or stopped by either changing the magnitude of the potential difference applied to the driving electrodes or by de-polarizing the ferroelectric member. For the present invention, the ferroelectric member can be depolarized by immersing the ferroelectric member in an alternating electric field of decreasing amplitude.

In another embodiment of the present invention, a first alternating current (AC) voltage source having an angular frequency, $\omega$, is connected to the polarizing electrode and activated to establish an alternating electric field in the ferroelectric member. Thus, a time-varying charge is placed on the contact surface of the ferroelectric member. In this embodiment, the driving electrodes are not in direct contact with the electrolyte solution. Rather, a layer of dielectric material is interposed between each electrode and the electrolyte solution. Also, for this embodiment, a second AC voltage source is connected to the driving electrodes to establish an alternating potential difference between the two driving electrodes. For the present invention, both the first and second AC voltage sources have the same angular frequency, $\omega$, but may differ in phase angle, $\phi$. Specifically, the phase difference, $\Delta\phi$, between the first and second AC voltage sources can be varied to control the flow rate of electrolyte solution in the conduit as well as the direction of flow. After the geometry of the device is established and the specific dielectric and ferroelectric materials have been selected, the relationship between flow rate and phase difference, $\Delta\phi$, can be calculated. In accordance with the present invention, the phase difference, $\Delta\phi$, can be varied to maximize the flow rate, reverse the flow direction or stop the flow of electrolyte solution in the conduit.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
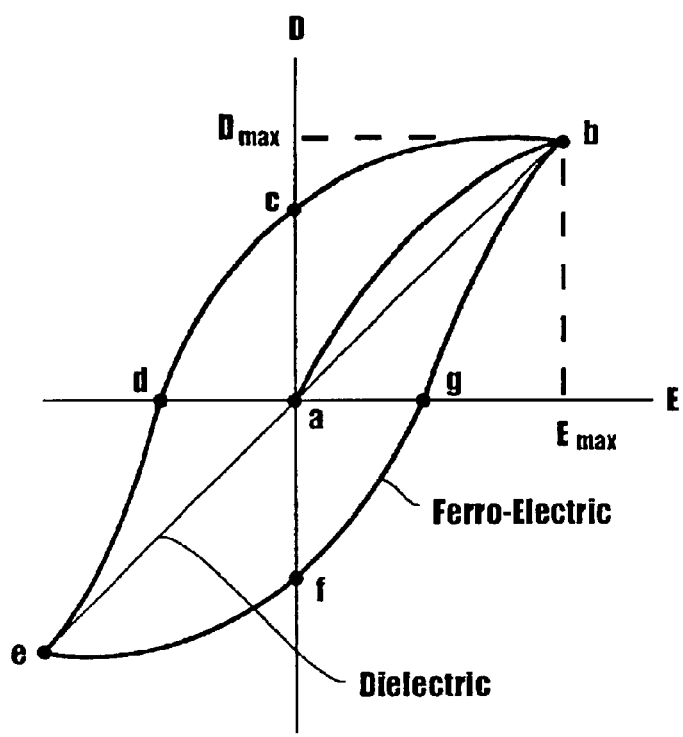
FIG. 1 is a plot of electric field, E, versus electrical displacement, D, for a typical ferroelectric material and a typical dielectric material.
Figure 2:
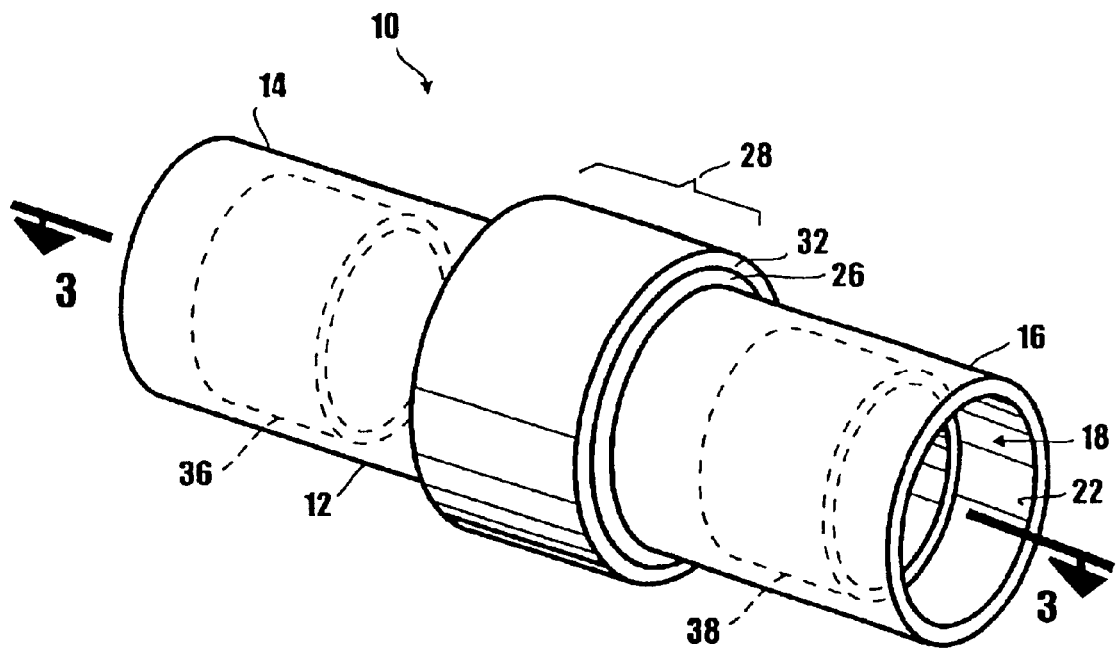
FIG. 2 is a perspective view of a ferroelectric electro-osmotic pump in accordance with the present invention.
Figure 3:
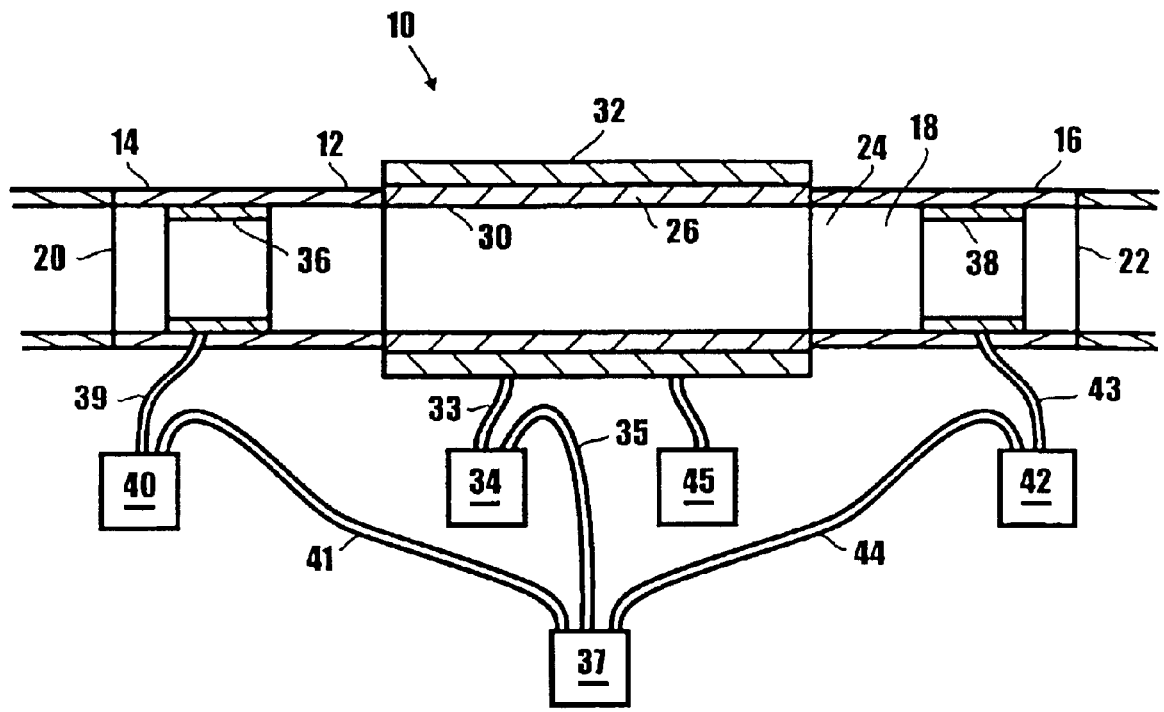
FIG. 3 is an elevational cross-section of the ferroelectric electro-osmotic pump shown in FIG. 2 as seen along line 3—3.

Referring to FIG. 2, a ferroelectric electro-osmotic pump in accordance with the present invention is shown and generally designated 10. As shown in FIG. 2, the pump 10 includes a conduit 12 having a first end 14, a second end 16 and a lumen 18 for containing an electrolyte solution. Although the conduit 12 is shown as a hollow, elongated cylinder, it is to be appreciated that the size and shape of the conduit 12 shown is merely exemplary, and that the conduit 12 can be formed as a tube, pipe, open-channel or internal passageway having any type of size, shape and cross-sectional characteristics. With cross reference to FIGS. 2 and 3, it can be seen that an opening 20, 22 is provided at each end 14, 16 of the conduit 12 to allow electrolyte solution 24 to enter and exit the lumen 18 of the conduit 12. As such, the conduit 12 can be connected in fluid communication at the ends 14, 16 with other fluid components (not shown). As shown, the pump 10 further includes a ferroelectric member 26 that is disposed along a portion 28 of the conduit 12. As shown in FIG. 2, the portion 28 is located between the ends 14, 16 of the conduit 12. For the present invention, the ferroelectric member 26 is formed with a contact surface 30 for interaction with the electrolyte solution 24, as shown in FIG. 3. Although the ferroelectric member 26 is shown as a hollow cylinder, it is to be appreciated that the size and shape of the ferroelectric member 26 shown is merely exemplary, and that the ferroelectric member 26 can be formed as a flat sheet, a projection, or any other shape which can accommodate a surface charge in response to an electric field. For the present invention, the ferroelectric member 26 is made from a ferroelectric material such as a metal titanate, a metal tantalate, a metal niobate or a metal tungustate. As further shown in FIG. 3, the ferroelectric member 26 is positioned along a portion 28 of the conduit 12 and oriented to allow the contact surface 30 to interact with the electrolyte solution 24 in the lumen 18 of the conduit 12.

With cross reference to FIGS. 2 and 3, it can be seen that a polarizing electrode 32 is positioned adjacent to the ferroelectric member 26 to establish an electric field within the ferroelectric member 26. As shown, a direct current (DC) voltage source 34 having leads 33, 35 is provided to establish an electric field in the ferroelectric member 26 to polarize the ferroelectric member 26. As shown, lead 33 of the voltage source 34 is connected to the polarizing electrode 32 and lead 35 connects the voltage source 34 to the common terminal 37. As shown, the polarizing electrode 32 is configured and oriented relative to the ferroelectric member 26 to establish a charge on the contact surface 30 of the ferroelectric member 26 when the ferroelectric member 26 is polarized. The polarity and magnitude of the charge placed on the contact surface 30 will depend on the polarity and magnitude of the voltage supplied to the polarizing electrode 32 and the type of ferroelectric material used to construct the ferroelectric member 26.

Also shown in FIGS. 2 and 3, driving electrodes 36, 38 are provided to establish a potential difference in the electrolyte solution 24. As shown, the driving electrodes 36, 38 are positioned along the conduit 12 to establish a potential difference across the portion 28 of conduit 12 containing the ferroelectric member 26. Specifically, driving electrode 36 is positioned between the first end 14 of the conduit 12 and the ferroelectric member 26, and driving electrode 38 is positioned between the second end 16 of the conduit 12 and the ferroelectric member 26. As shown, both driving electrodes 36, 38 are positioned for direct electrical contact with the electrolyte solution 24. Although the driving electrodes 36, 38 are shown as hollow cylinders, it is to be appreciated that the size and shape of the electrodes 36, 38 shown is merely exemplary, and that the electrodes 36, 38 can be any size or shape suitable for establishing a potential difference across the portion 28 of conduit 12. Further, as shown, a DC voltage source 40 having leads 39, 41 and DC voltage source 42 having leads 43, 44 are provided to establish a potential difference between driving electrode 36 and driving electrode 38. As shown, lead 39 is provided to electrically connect the voltage source 40 to the driving electrode 36 while lead 41 is connected to the common terminal 37. Similarly, lead 43 is provided to electrically connect the voltage source 42 to the driving electrode 38 while lead 44 is connected to the common terminal 37. The common terminal 37 electrically connects lead 35, lead 41 and lead 44 thus establishing a common potential for voltage sources 34, 40 and 42. It is to be appreciated that terminal 37 can be grounded to thereby ground leads 35, 41, 44, or can be used to provide a series connection between voltage source 40 and voltage source 42. Once established, the potential differential between electrodes 36, 38 creates a potential difference in the electrolyte solution 24 across the portion 28 of conduit 12 that contains the ferroelectric member 26. The potential difference in the electrolyte solution 24, in turn, applies a force on the charged ions in the electrolyte solution 24.

In operation, the DC voltage source 34 is activated to polarize the ferroelectric member 26 and thereby create a charge on the contact surface 30 of the ferroelectric member 26. Next, the first DC voltage source 34 can be deactivated, leaving the ferroelectric member 26 in the 'poled' state having an internal electric field (remnant polarization). Ions in the electrolyte solution 24 having a charge polarity that is opposite to the charge polarity of the contact surface 30 of the ferroelectric member 26 will be attracted to the contact surface 30. Once the ferroelectric member 26 is 'poled', DC voltage sources 40, 42 can be activated to establish a potential difference in the electrolyte solution 24 across the portion 28 of the conduit 12 containing the ferroelectric member 26. Upon establishment of the potential difference in the electrolyte solution 24, the electrolyte solution 24 will flow along the conduit 12. The direction of flow can be reversed by reversing the polarity of the driving electrodes 36, 38. The flow can be slowed or stopped by either changing the magnitude of the potential difference applied to the driving electrodes 36, 38 or by de-polarizing the ferroelectric member 26. For the present invention, an alternating voltage source 45 can be electrically connected to the polarizing electrode 32 to de-polarize the ferroelectric member 26. Specifically, the alternating voltage source 45 can be used to immerse the ferroelectric member 26 in an alternating electric field of decreasing amplitude, and thus de-polarize the ferroelectric member 26.

Figure 4:
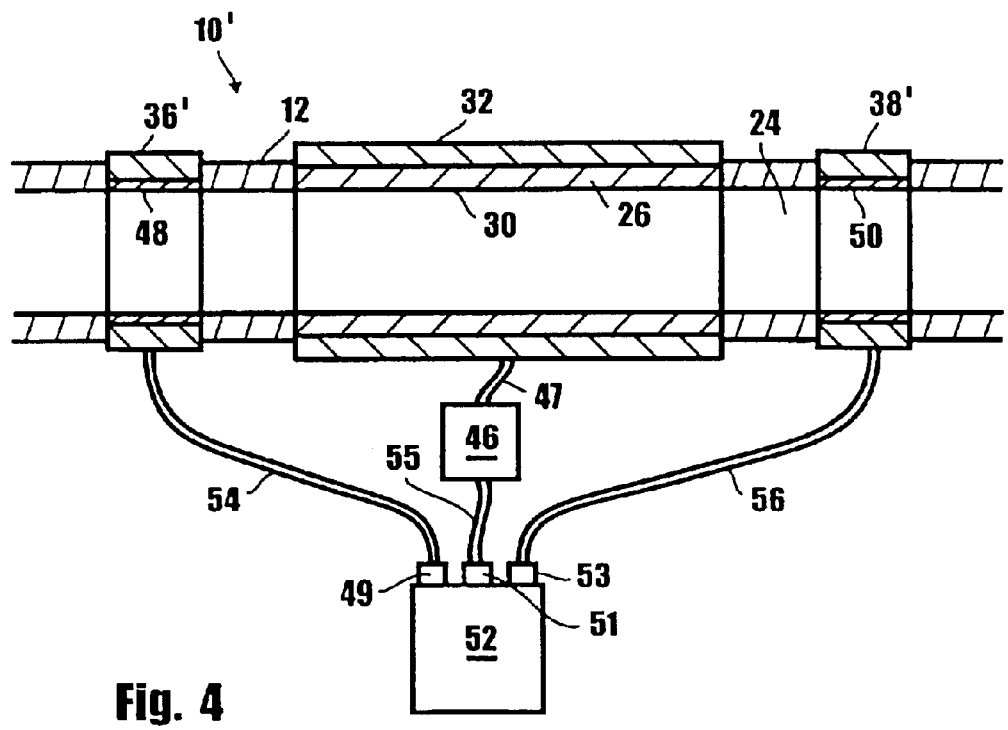
FIG. 4 is an elevational cross-section as in FIG. 3, showing another embodiment of a ferroelectric electro-osmotic pump in accordance with the present invention.

FIG. 4 shows another embodiment of a pump 10' in accordance with the present invention in which an alternating current (AC) voltage source 46 having an angular frequency, ω, is connected to the polarizing electrode 32 via lead 47. For the present invention, the AC voltage source 46 can be activated to establish an alternating electric field in the ferroelectric member 26. The alternating electric field, in turn, produces a time-varying charge on the contact surface 30 of the ferroelectric member 26. Also shown in FIG. 4, in this embodiment, a layer of dielectric material 48 is interposed between electrode 36' and the electrolyte solution 24. Similarly, a layer of dielectric material 50 is interposed between electrode 38' and the electrolyte solution 24. Thus, in this embodiment, the driving electrodes 36', 38' are not in direct contact with the electrolyte solution 24. Also, for this embodiment, an AC voltage source 52 is used to establish an alternating potential difference between the driving electrodes 36', 38'. As shown, the AC voltage source 52 can be formed with three terminals 49, 51, 53 wherein terminal 51 is a centertap and accordingly, the voltage difference between terminal 49 and terminal 51 is maintained equal to the voltage difference between terminal 53 and terminal 51. For the present invention, terminal 51 can be held at the ground potential. As further shown, lead 54 is provided to connect terminal 49 of the AC voltage source 52 to driving electrode 36' and lead 56 is provided to connect terminal 51 of the AC voltage source 52 to driving electrode 38'. Also shown, lead 55 is provided to connect terminal 51 of AC voltage source 52 to AC voltage source 46. In this embodiment, both AC voltage source 52 and AC voltage source 46 have the same angular frequency, ω, but may differ in phase angle, φ. Specifically, for the present invention, the phase difference, Δφ, between the AC voltage source 52 and AC voltage source 46 can be varied to control the flow rate of electrolyte solution 24 in the conduit 12. After the geometry of the device is established and the specific dielectric and ferroelectric materials have been selected, the relationship between flow rate and phase difference, Δφ, can be calculated. In accordance with the present invention, the phase difference, Δφ, can be varied to maximize the flow rate, reverse the flow direction or stop the flow of electrolyte solution 24 in the conduit 12.

Figure 5:
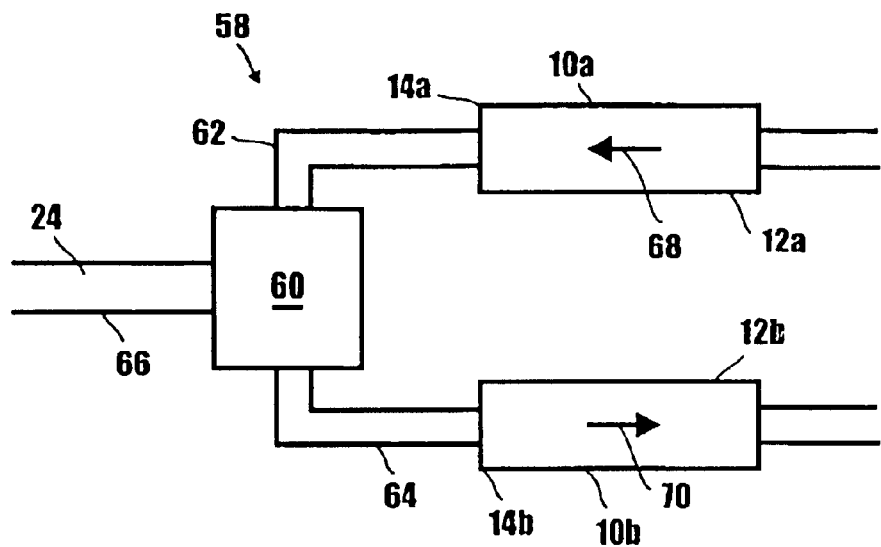
FIG. 5 is a schematic diagram of a switch that incorporates two ferroelectric electro-osmotic pumps.

Referring now to FIG. 5, a schematic diagram of a switch 58 having a first pump 10a and a second pump 10b is shown. It is to be appreciated that pumps 10a, b used in the switch 58 could be of the embodiment as shown in FIG. 3 (pump 10) or the embodiment as shown in FIG. 4 (pump 10'). Referring now to FIG. 5, it can be seen that the end 14a of the conduit 12a for pump 10a is plumbed to a junction 60 via pipe 62. Similarly, the end 14b of the conduit 12b for pump 10b is plumbed to the junction 60 via pipe 64. A pipe 66 is also plumbed to junction 60 as shown. Electrolyte solution 24 entering the junction 60 from pipe 66 can be routed through either pump 10a or pump 10b. Conversely, switch 58 can be used to select between electrolyte solution 24 flowing towards junction 60 through pump 10a or electrolyte solution 24 flowing towards junction 60 through pump 10b. For example, to route the electrolyte solution 24 from pipe 66 through pump 10a, the driving voltage and polarizing voltage for pump 10a are configured to cause electrolyte solution 24 to flow in the direction of arrow 68. Similarly, the driving voltage and polarizing voltage for pump 10b are configured to cause electrolyte solution 24 to flow in the direction of arrow 70. If DC voltages are used, the polarity of the applied voltages establishes the direction of flow. If AC voltages are used, the phase difference, Δφ, between the driving voltage and the polarizing voltage establishes the direction of flow. Although not shown, it is to be appreciated that the polarizing and driving voltages for pumps 10a and 10b could also be configured to route electrolyte solution 24 from junction 60 and through pump 10b. It is to be further appreciated that any number of pumps 10 could be plumbed into junction 60 for selective routing of electrolyte solution 24 along any number of routes.

Figure 6:
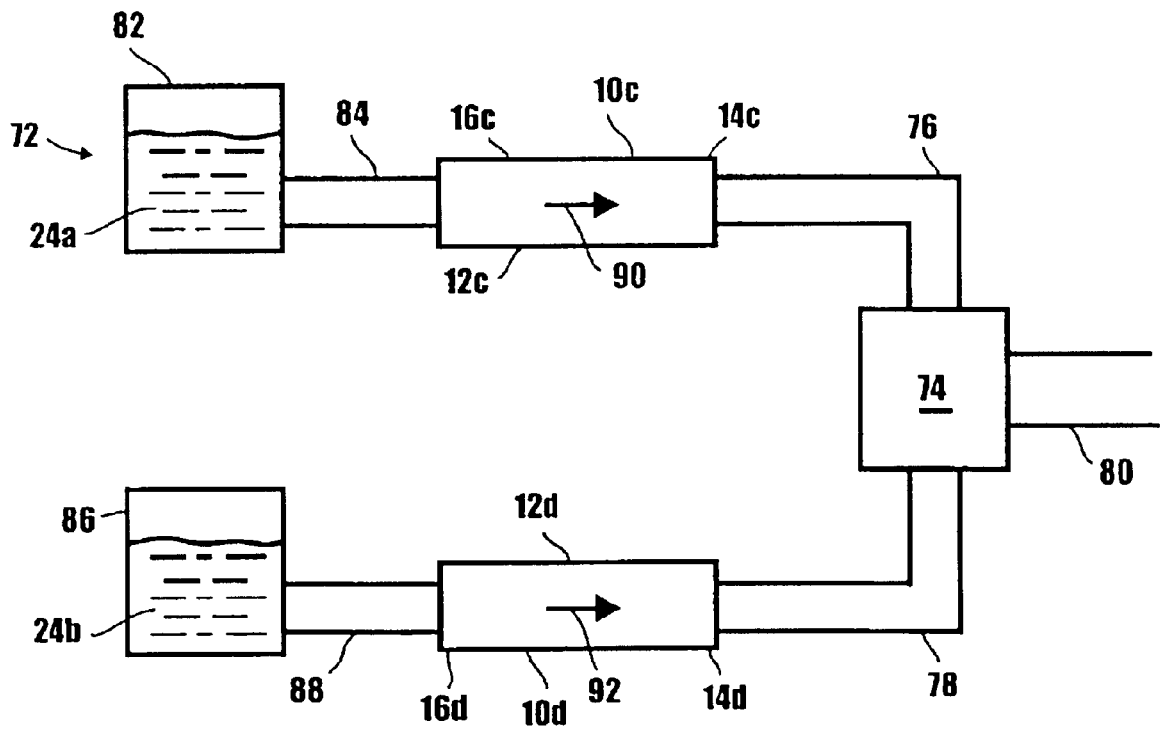
FIG. 6 is a schematic diagram of a mixer that incorporates two ferroelectric electro-osmotic pumps.

Referring now to FIG. 6, a schematic diagram of a mixer 72 having a first pump 10c and a second pump 10d is shown. It is to be appreciated that pumps 10c, d used in the mixer 72 could be of the embodiment as shown in FIG. 3 (pump 10) or the embodiment as shown in FIG. 4 (pump 10'). As shown in FIG. 6, the end 14c of the conduit 12c for pump 10c is plumbed to a junction 74 via pipe 76. Similarly, the end 14d of the conduit 12d for pump 10d is plumbed to the junction 74 via pipe 78. A pipe 80 is also plumbed to junction 74 as shown. A first reservoir 82 containing an electrolyte solution 24a is plumbed to the end 16c of conduit 12c for pump 10c via pipe 84 as shown. Similarly, a second reservoir 86 containing an electrolyte solution 24b is plumbed to the end 16d of conduit 12d for pump 10d via pipe 88.

In the operation of the mixer 72 shown in FIG. 6, the driving voltage and polarizing voltage for pump 10c are configured to cause electrolyte solution 24 to flow in the direction of arrow 90 and the driving voltage and polarizing voltage for pump 10d are configured to cause electrolyte solution 24 to flow in the direction of arrow 92. Further, these voltages can be adjusted to vary the flow rate of electrolyte solution 24 through the pumps 10c, d allowing for specific mixing proportions to be obtained at the junction 74.

While the particular device and methods as herein shown and disclosed in detail are fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for manipulating a solution along a fluid pathway, said solution having first ions and second ions, said first ions having a first charge polarity and said second ions having a charge polarity opposite said first ions, said method comprising the steps of:

providing a ferroelectric member having a surface;

placing said surface of said ferroelectric member in contact with said solution;

establishing a first electric field to polarize said ferroelectric member in a spontaneous poled state, and create a charge on said surface of said ferroelectric member to draw said first ions in a direction substantially perpendicular to the fluid pathway, towards said surface of said ferroelectric member; and establishing a second electric field within said solution substantially parallel to the fluid pathway to create a force on said second ions in the direction of said second electric field and cause said solution to flow in the direction of said second electric field.

2. A method as recited in claim 1 further comprising the step of:

establishing an alternating electric field of decreasing amplitude to de-polarize said ferroelectric member to cause said solution to stop flowing in the direction of said second electric field.

3. A method as recited in claim 1 wherein the magnitude of said first and second electric fields vary with time and have the same angular frequency.

* * * * *

UNITED STATES PATENT AND TRADEMARK OFFICE
CERTIFICATE OF CORRECTION

PATENT NO. : 6,805,783 B2  Page 1 of 1
DATED : October 19, 2004
INVENTOR(S) : Tihiro Ohkawa It is certified that error appears in the above-identified patent and that said Letters Patent is hereby corrected as shown below:

Column 4,
Line 26, delete "$\alpha=73.3°$" insert -- $\alpha=73.3^0$ --

Column 11,
Line 6, delete "member; and" insert -- member. --
Line 11, delete "field." insert -- field; and --
Line 12, insert -- removing said first electric field before establishing said second electric field. --

Signed and Sealed this

First Day of February, 2005

JON W. DUDAS
*Director of the United States Patent and Trademark Office*